United States Patent [19]
Dencks et al.

[11] Patent Number: 5,181,077
[45] Date of Patent: Jan. 19, 1993

[54] ATOMIC ABSORPTION SPECTROMETER

[75] Inventors: Carl G. Dencks; Gunther Roedel, both of Owingen, Fed. Rep. of Germany

[73] Assignee: Bodenseewerk Perkin-Elmer GmbH, Uberlingen, Fed. Rep. of Germany

[21] Appl. No.: 549,013

[22] PCT Filed: Mar. 13, 1989

[86] PCT No.: PCT/EP89/00260
§ 371 Date: Oct. 10, 1990
§ 102(e) Date: Oct. 10, 1990

[87] PCT Pub. No.: WO89/08832
PCT Pub. Date: Sep. 21, 1989

[30] Foreign Application Priority Data

Mar. 18, 1988 [DE] Fed. Rep. of Germany ....... 3809213

[51] Int. Cl.$^5$ .................. G01J 3/10; G01N 21/31; G01N 21/74
[52] U.S. Cl. .................................. 356/307; 356/312
[58] Field of Search ............... 356/307, 311, 312, 315, 356/316, 319

[56] References Cited

FOREIGN PATENT DOCUMENTS 2096315 10/1982 United Kingdom .

OTHER PUBLICATIONS

Liddell et al., *Analytical Chemistry*, vol. 52, No. 8, Jul. 1980, pp. 1256–1260.
Perkin–Elmer Advertisement, *Analytical Chemistry*, vol. 53, No. 3 Mar. 1981, p. 415A.
Applied Spectroscopy, vol. 27, No. 6, Nov.–Dec. 1973, D. L. Dick et al.: "Modification of an Atomic Absorption Unit for Dual Beam, Background Correction Measurements", pp. 467–470, see p. 467, left hand column, line 18—right hand column, line 35; Fig. 1.
Patent Abstracts of Japan, vol. 4, No. 100 (P-19) (582), Jul. 18, 1980 and JP, A, 5558419 (Hitachi Seisakusho K.K.) May 1, 1980, see abstract; Figs. 3,4.
TRAC. Trends in Analytical Chemistry, vol. 1, No. 9, May 1982, Elsevier Scientific Publishing Company (Cambridge, Great Britain), L. de Galan: "Zeeman Atomic Absorption Spectrometry", pp. 203–205, see Fig. 2; p. 204, left hand column, lines 24–35.
International Laboratory, vol. 17, No. 3, Apr. 1987 (Fairfield, Conn., U.S.) R. P. Liddell et al.: "The Effect of Background Correction Speed on the Accuracy of AA Measurements", pp. 82–87, see Fig. 1; p. 82, middle column, line 10—right hand column, line 13.

Primary Examiner—F. L. Evans
Attorney, Agent, or Firm—Edwin T. Grimes

[57] ABSTRACT

An atomic absorption spectrometer contains a line-emitting first light source (16), an official system (20, 22, 28, 30, 34) for generating a measuring light beam (18) which passes through a test sample space (12) and impinges on a photoelectric detector (38). An atomization device (14) for atomizing a test sample is so arranged in the test sample space that the constituents of the test sample are present in atomic form in an atomization region traversed by the measuring light beam (18). A light beam (72) is emitted continuously by a second light source (70). A beam splitter (74) reflects the light beam from the second light source (70) as a reference beam into the optical path of the measuring light beam (18). The two light sources (16, 70) can be switched on alternately by switching means. The beam splitter (74) can be removed optionally from the optical path. In addition, an electromagnet (44) generates a magnetic field aligned with the measuring light beam (18) at the site of the atomized test sample for optional background measurement by means of the longitudinal Zeeman effect.

1 Claim, 1 Drawing Sheet

ATOMIC ABSORPTION SPECTROMETER

The invention relates to an atomic absorption spectrometer comprising (a) a line emitting first light source, (b) an optical system for generating a measuring light beam, this measuring light beam passing through a sample cavity and impinging on a photo-electrical detector, (c) an atomizing device arranged in the sample cavity for atomizing a sample such that the components of the sample are present in atomic state in an atomizing area passed-through by the measuring light beam, (d) a second light source emitting a continuum, from which light source a light beam originates, (e) a beam splitter optionally removable from the path of rays, which beam splitter is arranged to reflect the light beam from the second light source into the path of rays of the measuring light beam as reference light beam, and (f) switching means which are arranged to switch on the two light sources alternately.

Atomic absorption spectrometers serve for determining the amount or concentration of an element looked for in a sample. For this purpose a measuring light beam from a line-emitting light source, a hollow cathode lamp for example, is directed to a photo-electrical detector. An atomizing device is arranged in the path of rays of this measuring light beam. The sample to be analyzed is atomized in this atomizing device such that the components of the sample are present in atomic state. The measuring light beam contains the resonant lines of the element looked for. These resonant lines of the measuring light beam are absorbed by the atoms of the element looked-for in the cloud of atoms, while ideally the other elements contained in the sample do not influence the measuring light beam. Therefore the measuring light beam is subjected to an attenuation which is a measure of the number of the atoms looked-for in the path of the measuring light beam and thus a measure of the concentration or the amount of the looked-for element in the sample, depending on the method of atomization applied. The absorption to which the measuring light beam is subjected is not only effected by the atoms of the element looked for. There is a "background absorption" due to the absorption of the light by molecules, for example. This background absorption has to be compensated for particularly highly sensitive measurements.

A flame may serve as atomizing device into which a sample is sparyed in as a solution. For highly sensitive measurements the electrothermal atomization is preferably used: The sample is introduced into a furnace which is heated to high temperature by passing electrical current therethrough. Thereby the sample is dried, at first, then charred and, eventually, atomized. Then a "cloud of atoms" is generated in the furnace in which cloud the element looked-for is present in atomic state. The measuring light beam is passed through this furnace. These furnaces can have different shapes. Conventionally they are made of graphite.

The invention relates to the background compensation with such an atomic absorption spectrometer.

BACKGROUND ART

Substantially two methods are used determining and compensating for background absorption. With one method, a reference light beam originating from a light source emitting a continuum with a relatively large bandwidth as compared to the line width is directed through the flame or cloud of atoms alternately with the measuring light beam, the absorption due to the atomic absorption plus background absorption, while the absorption of the reference light beam virtually is determined only by the background absorption (DE-A-1,911,048).

Atomic absorption spectrometers are known wherein a measuring light beam originates from a line emitting light source and is directed through a flame or a furnace for the electrothermal atomization to a detector and wherein a reference light beam originating from a light source emitting a continuum becomes effective alternately with this measuring light beam containing a line spectrum of an element looked for. This reference light beam is reflected into the path of rays of the measuring light beam by means of a beam splitter. The beam splitter usually is a partially transparent mirror. This mirror has reflecting and transparent areas uniformly distributed, such that 50% of the measuring light beam pass through the transparent surface portions and 50% of the reference light beam are reflected in the direction of the measuring light beam by the reflecting surface portions. The alternation between measuring light beam and reference light beam is achieved in that both light sources are switched on alternately. ("Applied Spectroscopy" Vol. 27, No. 6 (1973), 467–470).

In this prior art arrangement each light beam is attenuated by 50%. This results in deterioration of the signal-to-noise-ratio which may be critical with very sensitive measurements.

Furthermore it is known to leave a glass plate arranged in the bisecting line of the angle of the beam axes of hollow cathode lamp and deuterium lamp transparent on one surface portion and to provide it with a partially reflecting layer on another surface portion. The glass plate can be displaced in its plane, whereby optionally either both light beams fall on the partially reflecting layer and their paths of rays are superimposed, or only the light beam from the hollow cathode lamp passes through the transparent portion of the glass plate and falls onto a photometer. Then the instrument can optionally be used as a single beam photometer (JP-A-55 419; "Patent Abstracts of Japan" Vol. 4, No 100 (P-19), (582), 18.07. 1980).

Another method for determining the background absorption is based on Zeeman's effect: By applying a magnetic field to the sample the absorption line of the looked-for element in the sample is shifted relative to the spectral lines of the measuring light beam, such that there is no atomic absorption with the magnetic field applied and only background absorption is measured. The atomic absorption corrected for the background absorption can be measured by switching the magnetic field on or off.

The invention relates to an atomic absorption spectrometer in which the background absorption is determined by means of a reference light beam from light source emitting a continuum.

From German Patent Application 1,964,469 an atomic absorption spectrometer is known in which the radiation originates from a single light source designed as a line emitter, the radiation of which passing through the sample is frequency modulated by use of the longitudinal Zeeman's effect. In this prior art atomic absorption spectrometer, a hollow cathode lamp is arranged between the pole pieces of a solenoid. One of the pole pieces has a bore through which the measuring light beam passes through a flame serving as atomizing device and a monochromator and impinges upon a photoelectrical detector. The solenoid is arranged to be switched on and off, whereby the atomic absorption of the sample atoms compensated for the background absorption can be determined from the difference of the signals with the solenoid switched off and switched on. The windings of the solenoid are provided on the pole pieces.

In this prior art atomic absorption spectrometer the emission lines of the line emitting light source are periodically shifted by Zeeman's effect and thus the emitted light frequency is modulated and not the absorption lines of the sample.

From German patent 2,165,106 it is known to apply the magnetic field of a solenoid arranged to be switched on and off to the atomizing device, i.e. to the sample which is to be atomized, instead of to the light source. Therein the atomizing device is a flame. The magnetic field is applied perpendicularly to the direction of propagation of the measuring light beam. A splitting of the absorption lines due to "transverse" Zeeman's effect is effected, which again causes a relative shift of the emission lines of the measuring light beam and of the absorption lines of the sample. Again it can be discriminated between atomic absorption by the atoms of the element looked for and non-specific background absorption by switching the magnetic field on and off.

When the transverse Zeeman's effect is used splitting of a spectral line is effected into a central line the wave length of which corresponds to the non-shifted wave length of the respective line with the magnetic field switched off and two side lines are shifted to longer and shorter wave length relative thereto. The central line and the side lines are polarized differently. Therefore the influence of the central line can be eliminated by a polarizer. Such a polarizer, however, causes a light loss of 50%.

GB-A-2,096,315 describes an atomic absorption spectrometer which uses a graphite tube for the electrothermal atomization of the sample. For background compensation, a solenoid energized by a.c. current is provided, which generates a magnetic field orthogonal to the beam axis of the measuring light beam. By the transverse Zeeman's effect the absorption lines are split into a central $\pi$-component which is located at the wavelength of the undisturbed absorption line, and $\sigma$-components shifted relative thereto. The $\pi$- and $\sigma$-components are differently polarized. A monochromator is adjusted to the undisturbed absorption line. There is no polarizer for the elimination of the $\sigma$-component.

The compensation of the background absorption by use of Zeeman's effect can present problems, if the background absorption varies quickly, as the frequency of the switching on and switching off of the magnetic field is limited due to the inductivity of the solenoid (International Laboratory" 17 (1987) No. 3).

The various possibilities of the Zeeman-AAS have been shown in a paper in "TRAC Trends in Analytical Chemistry" Vol. 1 (1982), May, No. 9, 203-205.

DISCLOSURE OF THE INVENTION

It is the object of the invention to enable greater flexibility in determining the background absorption with an instrument of the type mentioned heretofore, and to ensure operation with optimum signal level depending on the conditions present.

According to the invention this object is achieved by
(g) a solenoid arranged to be switched on and off and to generate a magnetic field parallel to the direction of the measuring light beam at the location of the atomized sample, whereby, with the solenoid switched on, line splitting of the absorption lines of the sample and thus shifting of this absorption line relative to the spectral lines of the measuring light beam is effected by the longitudinal Zeeman's effected.

It is then possible to work optionally with measurement and compensation of the background absorption by means of the light source emitting a continuum, an attenuation of the measuring light beam by beam splitters being tolerated. It is, however, also possible, if the background absorption does not vary particularly quickly, to carry out the measurement of the background absorption making use of Zeeman's effect, without the measuring light beam being additionally attenuated by a fixedly built-in beam splitter. When the longitudinal Zeeman's effect is used, no absorption line appears at the location of the original line. Thereby the attenuation caused by the polarizer with the transverse Zeeman's effect or the reduction of sensitivity obtained without polarizer are avoided.

An embodiment of the invention is described in greater detail hereinbelow with reference to the accompanying drawings.

BRIEF DESCRIPTION OF THE DRAWING

The FIGURE shows schematically the set-up of an atomic absorption spectrometer, wherein the background absorption is compensated by using the longitudinal Zeeman's effect.

PREFERRED EMBODIMENT OF THE INVENTION

Figure 1:
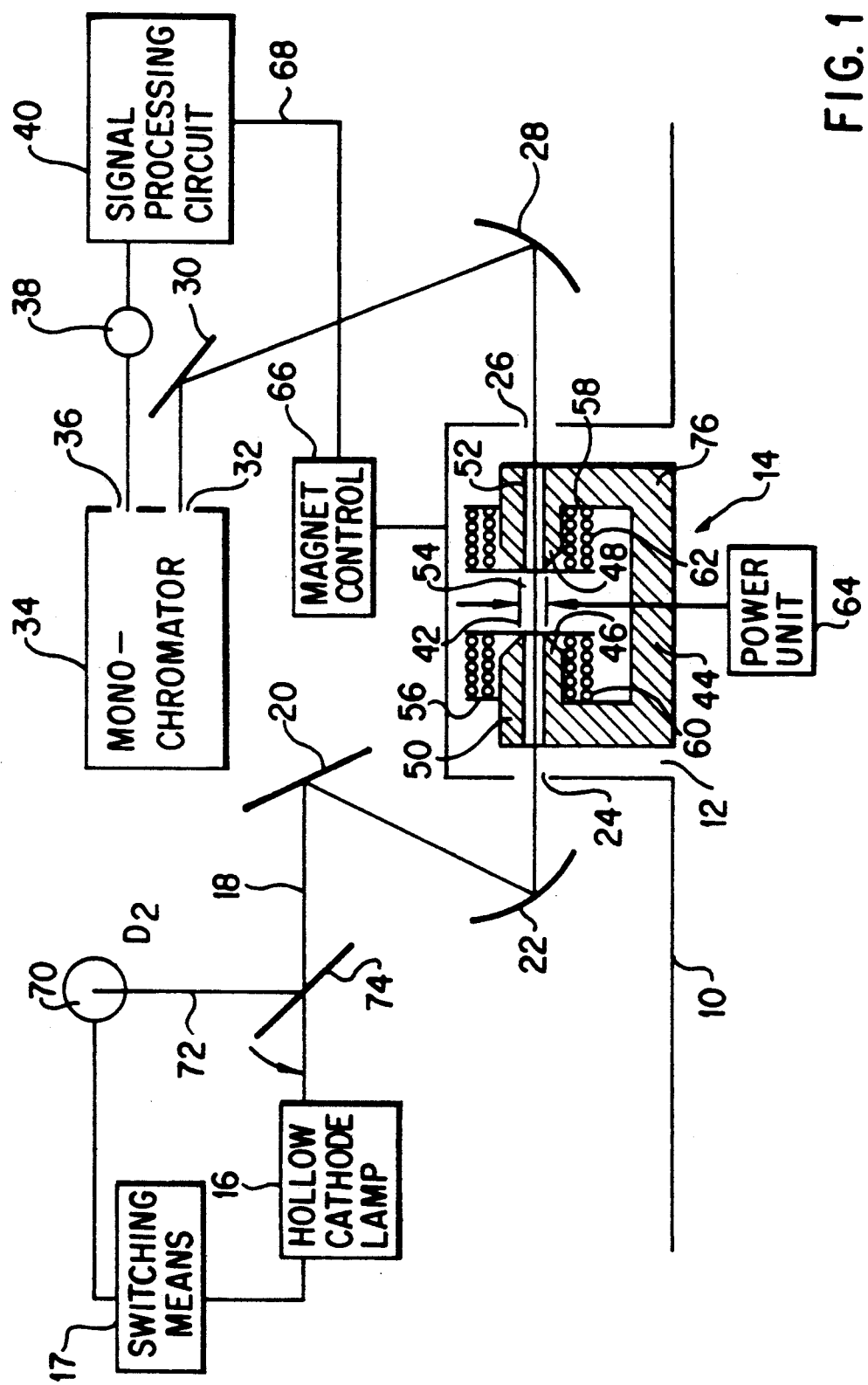

The FIGURE shows a schematical illustration of the atomic absorption spectrometer.

The atomic absorption spectrometer has a housing 10 in which the lamps, the optical system and the photosensitive detector are arranged. The housing 10 defines a sample cavity 12.

The atomic absorption spectrometer has a hollow cathode lamp 16 as a first light source 16. The light source 16 emits a line spectrum which corresponds to the resonant lines of a certain element looked for. A measuring light beam 18 originates from the light source 16. The measuring light beam 18 is deflected by a plane mirror 20 and focussed in the center of the sample cavity by a concave mirror 22 through an opening 24 of the housing 10. Then the measuring light beam passes through an opening 26 of the housing 10 aligned with the opening 24 and impinges upon a second concave mirror 28. The second concave mirror 28 focusses the measuring light beam 18 via a plane mirror 30 on the inlet slit 32 of a monochromator 34. A photoelectrical detector 38 is arranged behind an outlet slit 36 of the monochromator 34. The signal of the photoelectric detector 38 is supplied to a signal processing circuit 40.

The atomizing device 14 compriss a furnace for electrothermal atomization, only the actual furnace body 42 of the furnace device being illustrated in FIG. 1, and a solenoid 44 arranged to be switched on and off for the generation of a magnetic field at the location of the sample. The solenoid 44 has two aligned pole pieces 46 and 48 between which the furnace body is arranged. Aligned bores 50 and 52 are provided in the pole pieces 46 and 48. The bores 50 and 52 are aligned with a longitudinal bore 54 of the furnace body 42. The measuring light beam 18 passes through the bores 50 and 52 and through the longitudinal bore of the furnace body. Coil holders 56 and 58, respectively, are arranged on the pole pieces 50 and 52. Coils 60 and 62, respectively, of the solenoid 44 are wound on these coil holders 56 and 58. Numeral 64 designates a power unit which controls the current through the furnace body 42. As indicated the current is supplied transversely to the direction of the measuring light beam 18 and flows through the tubular furnace body 42 in circumferential direction. The solenoid 44 is controlled by a magnet control 66 such that the magnetic field alternately is switched on and off. At the location of the sample within the furnace body, the magnetic field of the solenoid 44 is in the direction of propagation of the measuring light beam 18. Therefore the longitudinal Zeeman's effect is generated at the sample atoms when the magnetic field is switched on. That means that the absorption lines of the sample atoms are split into two lines each, which are shifted relative to the undisturbed original absorption line. There is no atomic absorption in the sample at the wavelength of the original absorption line. Therefore also the atoms of the element looked for do not absorb the measuring light beam 18 because this measuring light beam contains only the non-shifted resonant lines characteristic of the element. Therefore only the background absorption is measured when the magnetic field is switched on. The component of genuine atomic absorption corrected for the background absorption can be determined from the measurements with the magnetic field switched on and off. For this purpose the cycle of switching the solenoid 44 on and off is supplied to the signal evaluation circuit 40 as indicated by a line 68. By the use of the longitudinal Zeeman's effect, a polarizer arranged in the path of rays can be omitted and the useful signal is improved.

A second light source 70 emitting a continuum is arranged in the housing 10. This second light source is a deuterium lamp. The second light source 70 emits a light beam 72. This light beam 72 from the second light source 70 can be deflected into the path of rays of the measuring light beam 18 via a beam splitter 74 which optionally is movable into the path of rays of the measuring light beam 18. The first and the second light sources 16 and 70, respectively, are arranged to be switched on alternately at a quick sequence by switching means 17 such that a measuring light beam 18 with a line spectrum from the first light source (hollow cathode lamp) 16 or a measuring light beam with a continuum from the second light source (deuterium lamp) passes alternately through the cloud of atoms generated in the furnace body. With this mode of operation with the beam splitter moved into the path of rays, the solenoid is switched off. Then the background absorption can be determined by measuring the absorption of the very narrow spectral line of the first light source and the absorption of a band of continuum radiation which is relatively wide as compared to the spectral line, and which is determined by the monochromator 34. The change between the first light source 16 and the second light source 70 is made at a frequency of more than 500 cycles per second, namely 1000 cycles per second. The mode of operation with a second light source emitting a continuum as reference light source permits detecting relatively quick changes of the background absorption, which could not be detected using Zeeman's effect by means of the solenoid 44. The solenoid 44 is relatively sluggish such that the frequency of the change between atomic absorption measurement and background measurement is limited. By the use of the longitudinal Zeeman's effect, no polarizer is required in the path of rays. Therefore, after the solenoid has been switched off, the atomic absorption spectrometer can operate with a second light source 70 emitting a continuum, without causing double attenuation of the light by the polarizer and additionally by the beam splitter 74.

It is, however, also possible to switch off the solenoid 44 and simultaneously move the beam splitter 74 out of the path of rays. In this case, operation is without background compensation but with the full intensity of the measuring light beam.

We claim:
1. Atomic absorption spectrometer comprising
   (a) a line emitting first light source (16),
   (b) an optical system (20, 22, 28, 30, 34) for generating a measuring light beam from said first light source which passes through a sample cavity in a predetermined direction for impinging on a photoelectric detector (38),
   (c) an atomizing device (14) arranged in the sample cavity for atomizing a sample such that the sample constituents are present in the atomic state in an atomizing area passed through by the measuring light beam,
   (d) a continuum emitting second light source (70) from which a light beam (72) originates for background correction,
   (e) a beam splitter (74) for reflecting, through the atomizing area and as a reference beam, the light beam originating from the second light source (70),
   (f) switching means for alternatingly switching on the two light sources (16, 70),
   (g) a Zeeman arrangement for background correction including an solenoid,
   (h) the solenoid being associated with the atomizing device for producing, in the atomizing area, a magnetic field extending substantially parallel to the predetermined direction of the measuring light beam and displacing the absorption lines of the sample atoms relative to the lines emitted by the first light source, due to the longitudinal Zeeman effect,
   (i) magnet control means for switching on and off the solenoid,
   (j) said beam splitter being movable into a moved-in operative position, in which the reference beam is directed through the atomizing area, and a moved-out inoperative position, and
   (k) the beam splitter and the solenoid constituting parts of alternative background correction means having selectively placed either (i) the beam splitter into the moved-in operative position and the solenoid into a switched-off deenergized condition or (ii) the beam splitter into the moved-out inoperative position and the solenoid into a switched-on energized condition.

* * * * *